April 16, 1963 C. FISCHER Plant Pat. 2,251
GLADIOLUS PLANT
Filed May 9, 1962
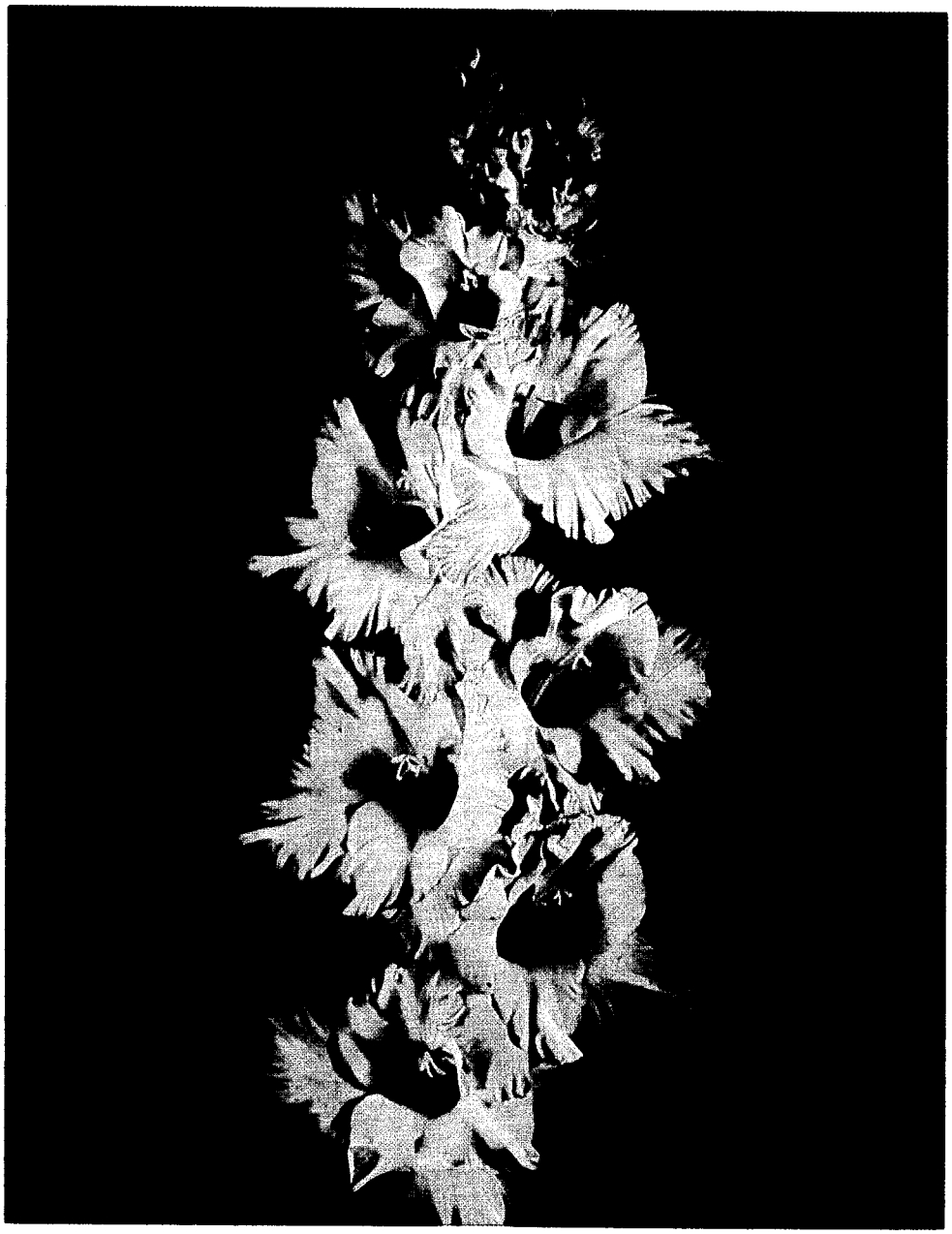
Inventor.
Carl Fischer
By: Robb & Robb
Attorneys.

United States Patent Office

Plant Pat. 2,251
Patented Apr. 16, 1963

2,251
GLADIOLUS PLANT

Carl Fischer, St. Charles, Minn., assignor to Imperial Flowers Limited, Leamington, Ontario, Canada, a corporation of Ontario Filed May 9, 1962, Ser. No. 193,637
1 Claim. (Cl. 47—60)

The present invention relates to a new and distinct variety of gladiolus plant which was originated by me by crossing two unnamed and unpatented gladiolus varieties of unidentified parentage.

The primary objective of this breeding was to produce a new gladiolus variety which constitutes an improvement over the variety known as "Corona" (unpatented). This objective was fully achieved by the breeding aforementioned, as performed by manual cross pollination in my outdoor breeding fields at St. Charles, Minnesota. The new variety is distinguished from its parents, as well as from all other varieties of which I am aware, as evidenced by the following outstanding features which represent a unique combination in gladiolus flower color:

(1) A distinctive and attractive cream or Naples Yellow general color tonality of the florets of the flower heads;

(2) A delicate rose or Spiraea Red edging of the petals of the florets; and (3) An intense, broad, sharp picotee form of the colored edging of the petals.

My new variety resembles the variety known as "Apple Blossom" (Plant Patent No. 1,517) more than any other, but differs therefrom principally by production of larger bulblets; a later blooming habit; a better flower opening habit from tight buds; a distinctive cream base color of the flowers, instead of the white base color of the flowers of "Apple Blossom"; and a broader and more intense red picotee edging of the flower petals.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Prolific propagator; produces extremely large bulblets; blossom spike averages between 60 inches and 62 inches in height.

Blooming habit: Early bloomer in the northern latitudes of the United States; comes into bloom in about 70 to 75 days from planting of large bulbs.

Stems: Tall; straight; stiff.
*Diameter at base.*—⅜ inch.
*Color (just above the bulb).*—Roseine Purple, Plate 629/3.

Foliage: Healthy; very upright; fan-shaped; average leaves range from 1½ inches to 1¾ inches wide; attains height of about 40 inches. Color—green, with mottling and varying shades of light yellow.

Disease resistance: Very resistant to Fusarium yellows, Sclerotina dry rot and Septoria leaf spot, as determined by comparison with other varieties grown in my fields near St. Charles, Minnesota, in irrigated black loam soil.

Corms (bulbs): Plump; heavily husked, with husk having a faint Rose cast and covering the corm well.
*Size.*—Average 2 inches in diameter.
*Color of flesh.*—Amber Yellow, Plate 505/1.

*Flower*

Spike: Tall; willowy; bears from 16 to 18 buds, with 5 or 6 buds usually open at one time, and with 6 buds showing color; flower head averages from 22 inches to 24 inches long.

Bud:
*Size.*—About 3½ inches long when opening.
*Opening.*—Usually 6 buds show color at one time; opens well.

Flower:
*Arrangement.*—Florets are informally arranged on the stem and usually all face forward.
*Size.*—Individual florets average 5½ inches in diameter, with upper blooms being progressively smaller.
*Form.*—Florets are somewhat triangular, needle-pointed and ruffled.
*Keeping qualities.*—Keeps well.

Petals:
*Shape.*—Ruffled; triangular; needle-pointed.
*Size.*—Outer petals—2½ inches wide. Inner petals—2¼ inches wide.
*Aspect.*—Heavy substance; smooth surface; ruffled at edges.
*Fragrance.*—None.
*Color.*—Base color representing heart of flower is cream or Naples Yellow, Plate 403/3, with picotee edging on outer edges of petals in the red color range generally corresponding to delicate rose or pink, and usually corresponding to Spiraea Red, Plate 025/1; opening buds are a deeper cream in base color.

*Reproductive Organs*

Stamens: Color—Veronica Violet, Plate 639/2.
Pistil: Color—white.

I claim:

A new and distinct variety of gladiolus plant, substantially as herein shown and described, characterized particularly as to novelty by the unique combination of a distinctive and attractive cream or Naples Yellow general color tonality at the heart of the flowers, the petals of the individual florets having a delicate rose or pink edging corresponding to Spiraea Red, and said colored edging having the form of a broad, sharp picotee.

No references cited.